United States Patent [19]

Asakura et al.

[11] 4,403,038

[45] Sep. 6, 1983

[54] BUFFERED SERUM SUBSTITUTE FOR BLOOD OXYGEN ANALYZER

[76] Inventors: Toshio Asakura, 301 Maple Ave., Drexel Hill, Pa. 19026; Horst K. Blume, 3375 Hillcroft Rd., Huntingdon Valley, Pa. 19006

[21] Appl. No.: 298,974

[22] Filed: Sep. 3, 1981

Related U.S. Application Data

[60] Division of Ser. No. 28,790, Apr. 11, 1979, Pat. No. 4,304,488, which is a continuation-in-part of Ser. No. 845,686, Oct. 26, 1977, abandoned.

[51] Int. Cl.³ .................... C09K 3/00; G01N 33/96; G01N 33/50
[52] U.S. Cl. .......................................... 436/16; 435/2; 436/11; 436/18; 436/68; 424/101
[58] Field of Search .................. 436/11, 16, 18, 68; 435/2; 424/101

[56] References Cited

U.S. PATENT DOCUMENTS

| | | | |
|---|---|---|---|
| 3,779,708 | 12/1973 | Runck et al. | 436/11 |
| 3,839,178 | 10/1974 | Macur | 436/11 |
| 3,914,400 | 10/1975 | Shulman et al. | 426/18 |
| 3,920,400 | 11/1975 | Scheibe et al. | 436/18 |
| 3,973,913 | 1/1976 | Louderback | 436/18 |
| 4,001,142 | 1/1977 | Turner | 436/11 |
| 4,102,810 | 7/1978 | Armstrong | 436/17 |
| 4,122,250 | 10/1978 | Schmer | 436/18 |
| 4,163,734 | 8/1979 | Sorensen et al. | 436/11 |
| 4,185,964 | 1/1980 | Lancaster | 436/18 |
| 4,289,756 | 9/1981 | Zimmermann et al. | 436/17 |
| 4,372,874 | 2/1983 | Modrovich | 436/17 |

*Primary Examiner*—Teddy S. Gron
*Attorney, Agent, or Firm*—John J. Simkanich

[57] ABSTRACT

A method and system for measuring the oxygen carrying capacity of normal and abnormal hemoglobins and red cells under controlled pH, ionic strength, temperature and gas conditions is described. A blood sample and a physiologically balanced medium are placed in a cuvette and means are associated therewith for measuring the fractional saturation of the sample and the partial pressure of the oxygen (sometimes referred to as the oxygen tension) and provide output signals to an X-Y plotter for continuous recording. Preferably, means for maintaining the temperature of the medium and the blood sample is provided.

2 Claims, 6 Drawing Figures

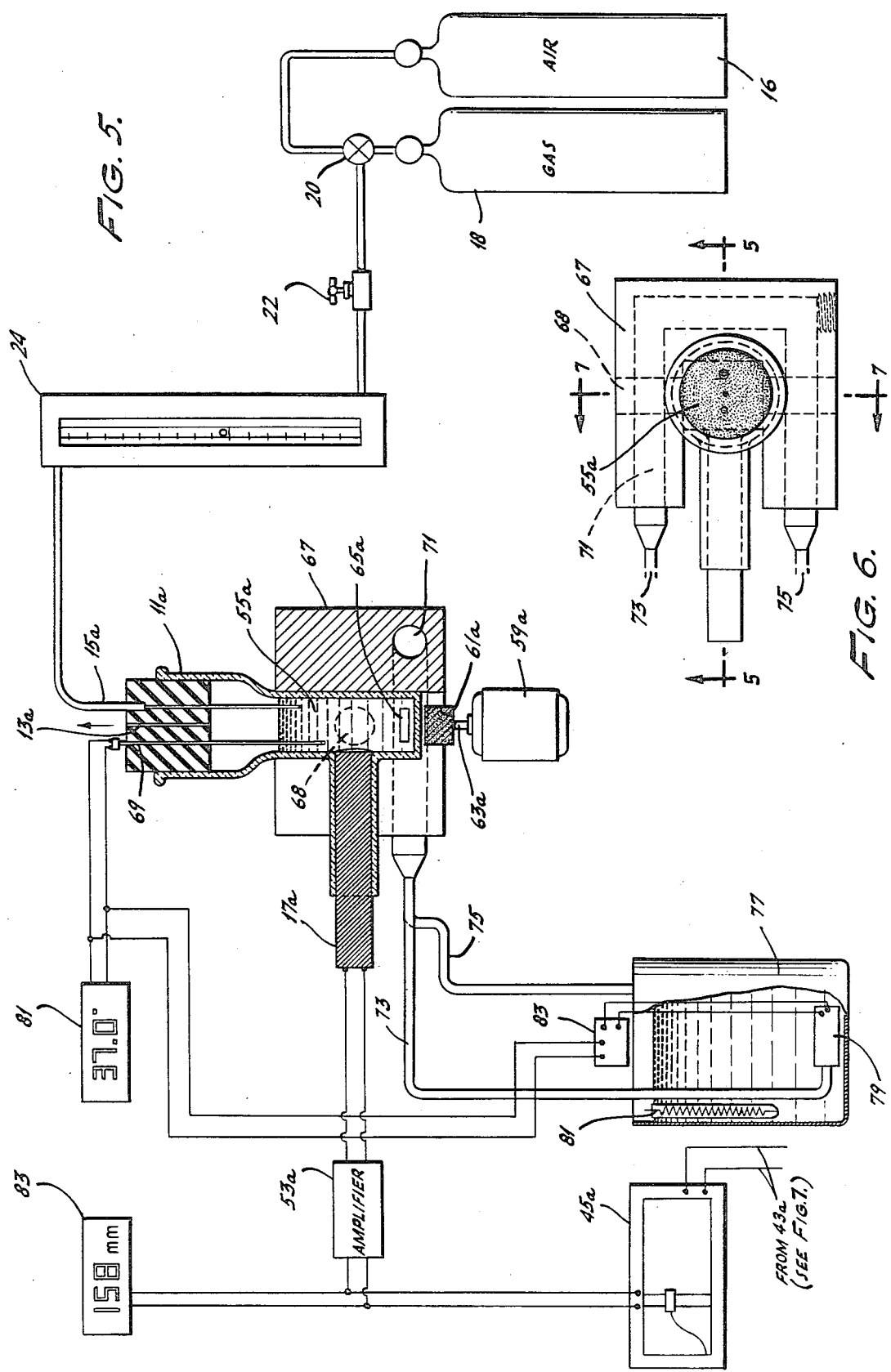

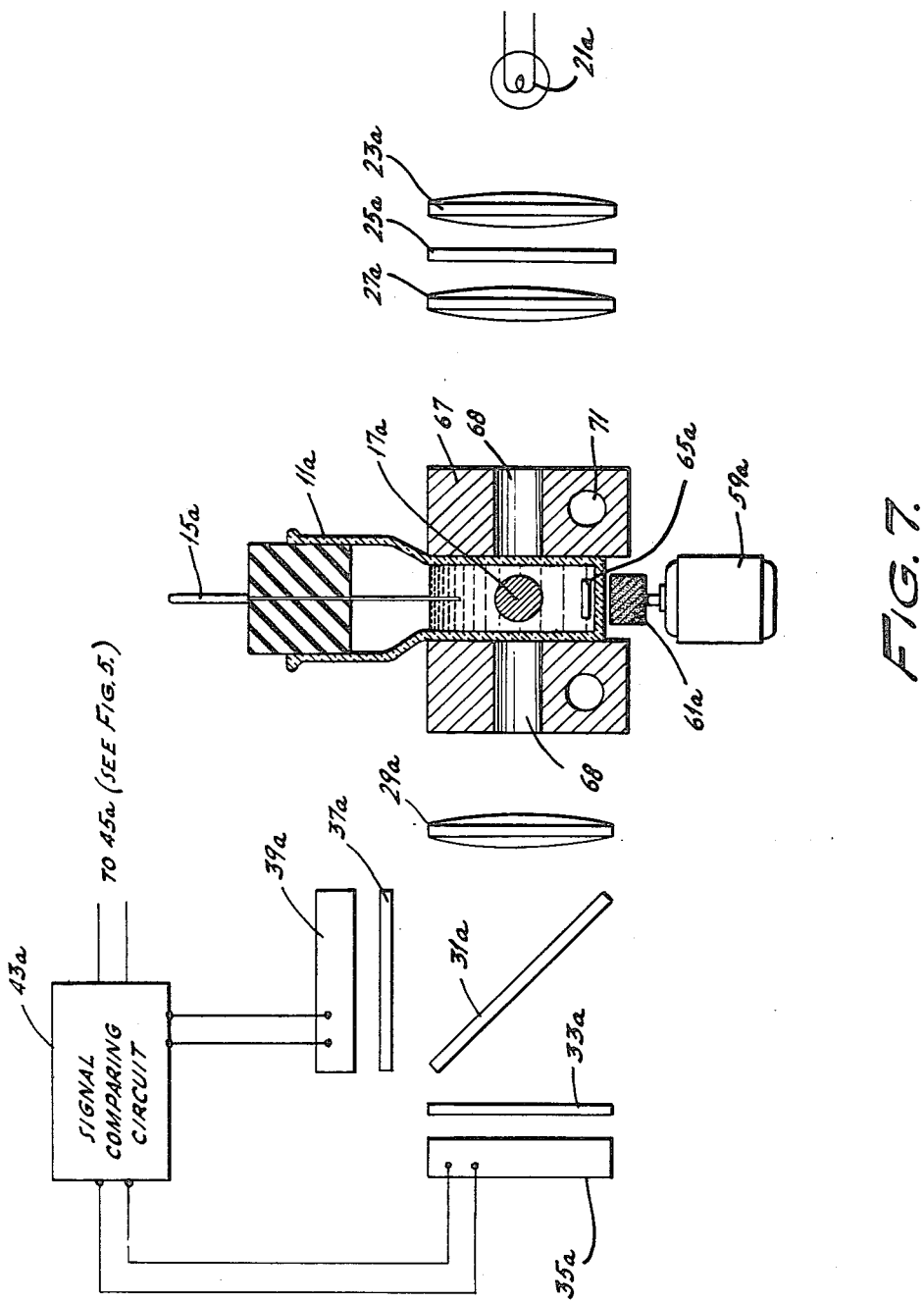

BUFFERED SERUM SUBSTITUTE FOR BLOOD OXYGEN ANALYZER

This is a division of application Ser. No. 28,790, filed Apr. 11, 1979 now U.S. Pat. No. 4,304,488 which is a continuation-in-part of application Ser. No. 845,686 filed Oct. 26, 1977, now abandoned.

The present invention relates to the measurement of the oxygen exchange property of normal and abnormal red cell hemoglobin in whole blood or hemolysate. More particularly, it relates to the measuring and plotting, at relatively high speeds, of the change in blood oxygen partial pressure to which the blood sample is subjected.

The most important function of blood is to deliver a sufficient amount of oxygen from the lungs to the tissues. In order to deliver oxygen most efficiently, hemoglobin in red blood cells must have an appropriate affinity for oxygen. If red cell hemoglobin has too high an oxygen affinity, such hemoglobin will effectively bind oxygen at the lungs but since it binds too tightly with oxygen, red cells containing such hemoglobin will not release a sufficient amount of oxygen at the tissue. In contrast, if a hemoglobin has too low an affinity for oxygen, such blood will not be able to bind enough oxygen at the lung. In order to attain the most efficient oxygen delivering capacity, the body uses various mechanisms. Under various pathologic conditions, however, one or more of these mechanisms become abnormal and the oxygen delivering capacity of blood may be altered. Sometimes a patient can have an abnormal hemoglobin in which the oxygen binding property is altered due to genetic mutation. It is important to know the oxygen delivering capacity of patient's blood because when this function is critically disturbed, there is a life threatening situation and the patient must be treated as quickly as possible. It is also important to evaluate the oxygen delivering capacity of stored blood prior to transfusion since stored blood may have a decreased oxygen delivering capacity.

In the past, one method of investigating the blood oxygen dissociation characteristics was the Van Slyke/Neill manometric method, requiring laborious measurements and point by point plotting. This method is laborious and usually takes six to eight hours to secure six or eight separate points under one set of conditions. It has come to be recognized that dual-wave length spectrophotometry could be used to evaluate blood oxygen content, with simultaneous observation being made at two selected wave lengths, one of which is preferentially responsive to the red color characteristic of oxygen-laden blood or hemoglobin, the other being equally responsive to the light transmission characteristic of blood or hemoglobin which is either oxygen-laden or devoid of oxygen, the transmission of the light of the latter wave length being used as a reference base.

As of the time of preparation and execution of this patent application, blood oxygen association apparatus involving automatic X-Y plotting of a dissociation curve is known. However, the existing apparatus is vulnerable to changes of pH, ionic strength, temperature and gas conditions of the blood sample under investigation. Where whole blood is used as the specimen under spectrophotometric examination, it suffers the disadvantage that the pH of the sample cannot be adjusted to and held at a physiologically desired value. As a result, different test data could be yielded by different plots run on samples taken from the same blood specimen and the data obtained from these instruments must be corrected depending on the pH and other factors. Also, such a procedure is not believed to be suitable for reversal to perform a blood oxygen dissociation test—the converse of an association test. In some instances, it is desirable to provide a dissociation test and plot thereof in preference to an association test.

An object of the present invention is to provide superior test equipment and procedure for determination of the oxygen exchange property of hemoglobin.

Another object is to provide a system which is stable and adjustable with respect to pH of the sample under examination, and capable of producing, in a relatively short time, both the blood oxygen dissociation curve and the blood oxygen association curve under controlled pH, ionic strength and temperature.

One technique presently being used for blood oxygen dissociation analysis involves the use of a slide prepared with a thin smear of blood, covered over by a plastic membrane. This slide, when subjected to an atmosphere with progressively decreasing oxygen content, tends to show a spectrophotometric change of its absorbance characteristic which may be due in whole or in part to drying of the blood sample. The changes in pH, ionic strength and temperature are, however, totally uncontrolled.

In accordance with one feature of the present invention, a minute blood sample to be tested is put into a specially prepared serum substitute so that the blood is placed under physiologic conditions. The vessel in which this solution is contained is provided with agitation means; oxygen partial pressure measuring means, and an arrangement for changing oxygen content within the vessel. Light transmitted through the liquid contained in this vessel is subjected to photometric analysis involving a comparison of the light intensities at two selected wave lengths. By plotting the resultant photometric measurement against the oxygen partial pressure, one is provided with a curve showing the performance of the blood sample with respect to its oxygen association or dissociation characteristics. The process may be run each way, demonstrating minimum hysteresis and maximum reproducibility of blood oxygen dissociation and association tests. Preferably, means for maintaining the temperature of the blood sample-serum is also provided.

This invention will be better understood by reference to the following description considered in connection with the accompanying drawings, wherein:

FIG. 5 is a general view, partly in section, showing another embodiment of apparatus in accordance with this invention;

FIG. 6 is a plan view of a cuvette and heating means usable in accordance with this invention; and FIG. 7 is a view, partly in section, illustrating the apparatus of FIG. 5 with associated dual wave length spectrophotometer.

Figure 1:
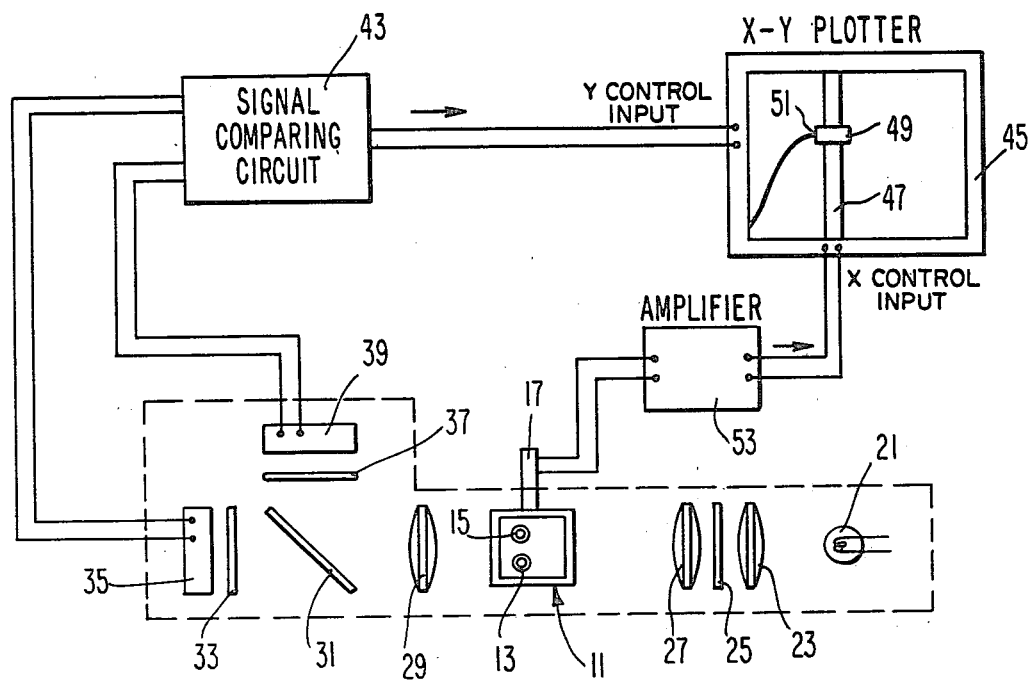
FIG. 1 is a general view of the blood oxygen dissociation analysis apparatus of the present invention.
Figure 2:
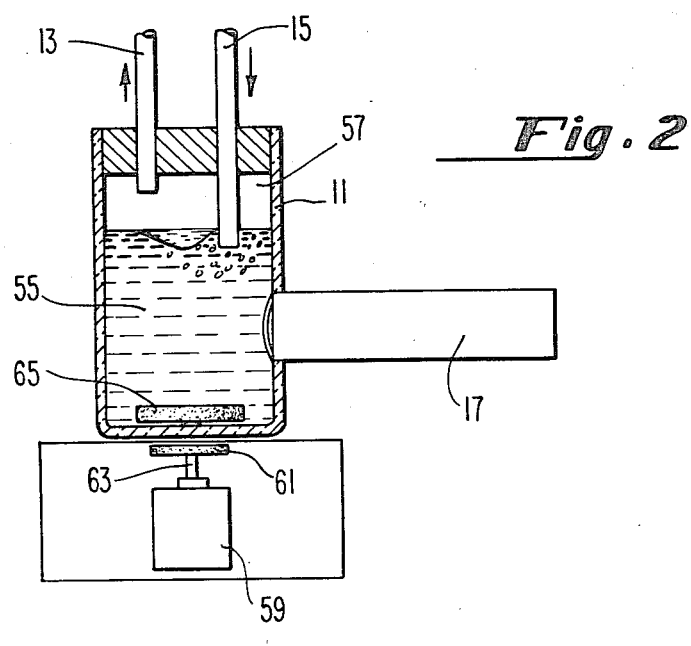
FIG. 2 is a schematic showing of the arrangement of the vessel, probe, agitator and gaseous exchange arrangement involved in the apparatus of FIG. 1.

Referring now to FIGS. 1 and 2, a transparent vessel 11 is provided for containing the blood sample in the specially prepared serum substitute solution. To this vessel 11 are connected gas exchange tubes 13 and 15, and a Clark electrode 17 for detecting the partial pressure of oxygen within the vessel 11.

A light source 21 is provided in the apparatus of FIG. 1, along with condensing lenses 23, 25 and 27. These direct a concentrated beam of light upon the vessel 11 to cause part of the incident light to be absorbed selectively by the solution in the vessel 11 and a further part to be transmitted through said solution to be detected and relied upon for blood oxygen analysis. Preferably this system should be arranged to direct the light through the solution at a position adjacent the Clark electrode 17.

The light passing through the solution contained in the vessel 11 proceeds through a further lens 29 to a semi-silvered mirror 31 which is positioned substantially at a 45° angle and arranged to reflect substantially half the light impinging thereon and to transmit substantially half the incident light arriving through lens 29. The transmitted half of the light proceeds through a selected filter 33 to a first photoelectric cell 35, and the reflected light proceeds through filter 37 to photoelectric cell 39.

Figure 3:
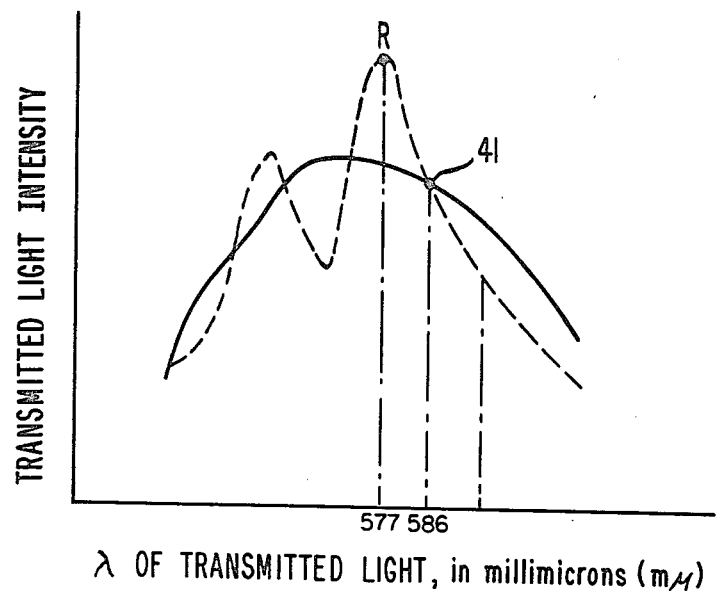
FIG. 3 is a graph of the light transmission characteristics of blood as a function of wavelength, in the presence or the absence of oxygen.

Referring to FIG. 3, one filter 33 is arranged to respond selectively to a strong component of light present in oxygen-rich red blood, for example, a wave length of 577 millimicrons as illustrated in FIG. 3. The other filter 37 is arranged to respond to a wave length of light at which the light transmitted through the solution is of about equal intensity whether the blood is oxygen enriched or deficient in oxygen as represented by point 41 in FIG. 3. An example of such a wave length is 586 millimicrons. The signal comparing circuit 43 in FIG. 1 responds by producing an increasing output as the output from photoelectric cell 35 increases relative to the output of the photoelectric cell 39 which is relied on for a reference level, and the thus varying signal output of comparing circuit 43 is supplied to the Y control input terminals of an X-Y plotter 45 having a servo-driven vertical element 47 and a servo-driven Y axis responder 49 carrying the stylus 51.

The output potential of the Clark electrode 17 varies in accordance with the partial pressure of oxygen contained within the vessel 11. The output from the Clark electrode 17 is amplified in amplifier 53 and the resulting output signal which varies as a function of the oxygen partial pressure is used to control the X control input circuit of the X-Y plotter 45.

The solution 55 contained within the vessel 11 is a physiologically balanced medium such as buffered serum substitute. Preferably, the solution 55 is a 0.9% saline solution containing 5 millimolar of sodium phosphate. One buffered serum substitute solution which has been found suitable is as follows:

| | |
|---|---|
| Sodium Chloride | 100 millimolar |
| Potassium Chloride | 5 millimolar |
| Imidazole Buffer | 30 millimolar |
| Sodium Phosphate | 5 millimolar |
| Glucose | 5 millimolar |

The imidazole component of this isotonic solution is a chemical compound listed in the Merck index. It provides for high stability of the pH, at 7.4 at 37° C. The Monograph for imidazole is number 4807, in the Ninth Edition of the Index, published 1976.

The dimensions of the vessel 11 may be of the order of 12.5 millimeters square in plan view and approximately 5 centimeters in height. The amount of the solution contained therein may be of the order of 4 milliliters. The solution in which is contained a drop of the patient's blood does not fill the entire space within the vessel 11, but leaves a volume of gas 57 at the top.

It is important that the solution be kept under moderate agitation. For this purpose, a motor 59 is arranged in the base of the vessel assembly, with a magnet 61 driven by the motor shaft 63. Magnet 61 imparts rotation to a companion magnet 65 arranged to revolve in the bottom of the vessel 11, its action being imparted by the coupling between said magnet 65 and the magnet 61 on the shaft of motor 59.

The motor 59 is caused to drive the magnets at such rate as to provide enough agitation in the solution to produce a distinct dip of the upper surface in the middle of the top of the solution 55, but not to develop a complete vortex down into the liquid. A suitable pattern of the dip of the liquid is shown in FIG. 2.

In order to provide for changing of the gas content in vessel 11 (either the replacement of an oxygen atmosphere with nitrogen, or the converse replacement of an inert gas such as nitrogen with oxygen), the gas which is desired to be introduced into the vessel is introduced through tube 15, with an outward flow of gas through tube 13. A test involving the introduction of oxygen is started with an air atmosphere. This may be done by opening the top of the vessel to expose it to the ambient air. Next, oxygen is introduced through tube 15 with the result that in a reasonable length of time, of the order of 30 seconds, the blood sample contained in the solution 55 will have been fully associated with oxygen. Nitrogen (or argon) is next introduced to remove oxygen from the hemoglobin. Twenty minutes may be required for this test. It has been found that for efficient introduction of gases into the solution, the lower end of the tubing 15 should extend slightly below the surface of the solution 55, so that the gas introduced through the tubing 15 is caused to proceed downward into the liquid from the end of tubing 15 and to bubble up through the liquid to its surface. A suitable rate of flow in the gas exchange is of the order of 1 to 20 cc. per minute, if some 20 minutes time is available for a test run.

By virtue of the use of a buffered serum substitute such as that herein described, including the imidazole buffer, the alkalinity of the solution contained in the blood sample is rendered substantially constant. This provides great stability for the running of the test with the X-Y plotter. It makes it possible to run two converse tests in succession, one being the plotting of the blood oxygen association curve, each curve plot requiring approximately 20 minutes.

One substantial benefit from the use of the system herein described is the wide range for selection of temperature and pH. This fact, coupled with the fact that only a very small sample of blood is required, renders the system suitable for use over a wide range of conditions, including the monitoring of the blood condition in a patient undergoing major medical treatment.

Figure 4:
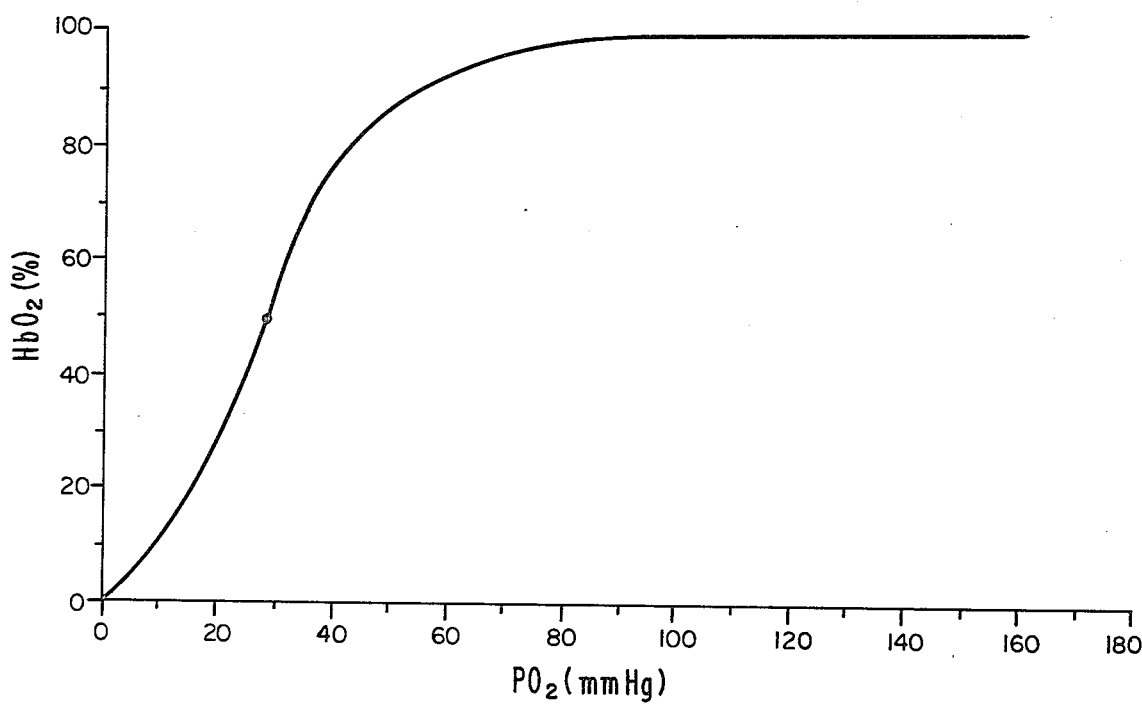
FIG. 4 is a graph diagrammatically illustrating the graphic output producible with the present invention.

An example of the type of curve produced in a given blood sample is shown in FIG. 4. The oxygen saturation of blood or hemoglobin in percentage of maximum is plotted against the partial pressure of oxygen in millimeters of mercury. A significant measurement is the oxygen partial pressure at which the blood oxygen has reached 50%, which in the example shown in FIG. 4 may be approximately 27 millimeters of mercury. This value is referred to as the "P 50" value for a given normal blood sample under analysis.

Referring now to FIGS. 5 and 6 of the drawing, there is illustrated another embodiment of the invention in which the blood sample is maintained under in vivo conditions during the testing. In describing this embodiment, parts like those illustrated in the embodiment of FIGS. 1 and 2 will be referred to with like reference numerals with the addition of the suffix a. A transparent vessel 11a is provided and is formed to be received in a heating block 67 which will be more fully explained hereinafter. To this vessel 11a are connected gas exchange tubes 13a, 15a, and a Clark electrode 17a, this electrode being operative to detect the partial pressure of oxygen within the solution. As in the embodiment of FIGS. 1 and 2, the Clark electrode 17a, outputs to an amplifier 53a, and the resulting output signal which varies as a function of the oxygen partial pressure is used to control the X control input circuit of the X-Y plotter 45a. The tube 13a functions as a vent and the tube 15a is coupled to either an air tank 16 or a gas tank 18 through a selector valve 20, adjustable needle valve 22 and a flow meter 24. Similar to the embodiment of FIGS. 1 and 2, agitation means including motor 59a, magnets 61a and 65a, and shaft 63a is provided to agitate the solution to provide a dip at the upper surface of the solution as described with respect to the embodiment of FIGS. 1 and 2.

A light source 21a along with condensing lenses 23a, 25a and 27a are arranged adjacent the vessel 11a to direct a concentrated beam of light upon the vessel and cause part of the incident light to be absorbed selectively by the solution in the vessel and a further part to be transmitted through the solution to be detected and relied upon for blood oxygen analysis. The light source 21a and its associated lenses are located externally of the vessel at a location whereby the light is at a right angle to the Clark electrode 17a and at a height such that the light path through the solution is adjacent the working face of the electrode 17a. To provide the necessary light path through the block 67, the parallel legs of the block are formed with through holes 68, 68 through which the light passes. As will be made clear both of the measurements are made in the same general portion of the solution so that differences that could occur by making each of the measurements at different locations are substantially eliminated.

As in the embodiment of FIGS. 1 and 2, this embodiment includes a lens 29a, a semi-silvered mirror 31a positioned at a 45° angle, a filter 33a, a first photoelectric cell 35a for receiving the transmitted light, a second filter 37a for receiving the reflected light and a second photoelectric cell 39a. The operation of this portion of the system and its associated signal-comparing circuitry 43a is similar to that described previously and will not be re-explained except to note that the output of the comparing circuit 43a is supplied to the Y control circuit of the X-Y plotter 45a.

The solution 55a within the vessel 11a is important to the function of the system and is the same solution described with respect to the embodiment of FIGS. 1 and 2. It is emphasized at this point that this solution has been found to provide a high stability of the pH of the solution at 7.4 at a temperature of 37° C., that is, the temperature of the human body. To maintain the temperature of the solution at a relatively constant temperature there is provided the heating block 67, a thermocouple 69 and associated apparatus. By maintaining the pH and temperature of the solution at a constant, testing of the blood sample in the buffered serum substitute solution will provide a high degree of accuracy for the curves obtained with this system and method. The heating block can be seen in FIG. 6 to be a generally U-shaped member which snuggly receives the lower portion of the vessel 11a. Preferably this lower section of the vessel 11a is rectangular so that its sidewalls are in full contact with the inner surfaces of the block 67. The heating block is preferably made of a metal, for example, aluminum, providing for good heat conductivity and is formed with a water passage 71 extending through each of the three legs. This water passage 71 can be formed by drilling an opening in each of the parallel legs of the block which terminates in the connecting leg. The connecting leg is further drilled from one end through to the passage in the other end and the opening in the outer wall can be plugged to prevent leakage. An inlet line 73 is connected to the opening in the water passage in one of the parallel legs and a discharge line 75 is connected to the opening in the other of the parallel legs and these lines are connected to a tank 77 which is filled with water.

Associated with the tank 77 is a suitable submersible pump 79, a submersible electric heater 81 and an electric controller 83. The water is heated and circulated through the water passage to maintain the temperature of the solution in the vessel 11a at a constant. This can be done by maintaining the temperature of the water in the tank 77 at a constant by utilizing a thermostat means for controlling the operation of the electric heater 81. The thermocouple 69 then provides a signal which is a function of the temperature of the solution in the vessel 11a, which is compared in the controller 83 with a set point signal, for example, a signal which is a function of 37° C. When the temperature of the solution drops below 37° C., then a signal from the controller 83 operates the pump 79 so that warm water is circulated through the passage 71 in the heating block 67, raising the temperature of the solution. When the temperature of the solution reaches 37° C., the controller 83 discontinues its output and the pump 79 is shut off. It should be understood that other systems can be used in accordance with this invention.

With this arrangement, in vivo conditions for the blood sample can be maintained. As noted previously, the buffered serum substitute into which the blood sample is introduced, is of a nature that the pH remains relatively constant as does the ionic strength. By utilizing the heater means to maintain the temperature of the solution at body temperature, the accuracy of the test results is enhanced and no subsequent corrections need be made thereto.

The thermocouple 69 can be any of a variety of conventional devices and can be connected to a digital readout thermometer 81 which displays the temperature of the solution. Similarly, the signal from the electrode 17a can be connected to a digital readout barometer 83 which displays the partial pressure of the oxygen.

When it is desired to run an oxygen association test, the blood sample is deoxygenated and the selector valve 20 and needle valve 22 are manipulated to allow air oxygen to flow into the vessel 11a. When it is desired to run an oxygen dissociation test, the blood sample is oxygenated and the selector valve 20 and needle valve 22 are manipulated to allow an inert gas such as nitrogen to flow into the vessel 11a. A significant advantage of the invention, however, is that the sample need not be oxygenated or deoxygenated prior to testing. It can initially be determined if the same is oxygenated; if so, a dissociation test is run; if not, an association test is run. In some instances it may be desirable to monitor the pH of the solution. If so, a pH probe may be located in the solution in vessel 11a and the pH can be continuously monitored and adjusted. The tests can be run in about twenty minutes with no special preparation of the blood and without the use of any special chemicals or gases. If desired, the association and dissociation test can be run on the same sample to check on each other. Correction of the result is minimized.

Whole in the foregoing there has been disclosed a preferred embodiment of the invention, it should be understood that various changes and modifications can be made within the true spirit and scope of the invention as recited in the appended claims.

What is claimed is:

1. A buffered serum substitute for receiving a blood sample, said serum substitute comprising a 0.9% saline solution containing 5 millimolar of sodium phosphate, sodium chloride, imidazole, potassium chloride, and glucose, to form a physiologically balanced medium.

2. A buffered serum substitute as defined in claim 1 wherein said components have a proportion in accordance with the following: sodium chloride, about 100 millimolar; imidazole, about 30 millimolar; potassium chloride, sodium phosphate and glucose, each about 5 millimolar.

* * * * *